United States Patent
Donahue

(10) Patent No.: US 9,415,248 B2
(45) Date of Patent: Aug. 16, 2016

(54) FIRE EXTINGUISHMENT CONTAINER

(75) Inventor: Thomas P. Donahue, Puyallup, WA (US)

(73) Assignee: The Boeing Company, Chicago, IL (US)

( * ) Notice: Subject to any disclaimer, the term of this patent is extended or adjusted under 35 U.S.C. 154(b) by 778 days.

(21) Appl. No.: 13/439,928

(22) Filed: Apr. 5, 2012

(65) Prior Publication Data

US 2013/0264346 A1    Oct. 10, 2013

(51) Int. Cl.
*B65D 90/22* (2006.01)
*A62C 3/16* (2006.01)

(52) U.S. Cl.
CPC ............... *A62C 3/16* (2013.01); *A61K 2300/00* (2013.01)

(58) Field of Classification Search
CPC ... B64D 37/06; A61K 2300/00; A61K 45/06; B65D 81/02
USPC ........... 220/501, 502, 526, 560.01, 798, 88.1; 206/219, 221, 263
See application file for complete search history.

(56) References Cited

U.S. PATENT DOCUMENTS

| | | | |
|---|---|---|---|
| 1,832,056 A * | 11/1931 | Spencer | 169/26 |
| 2,793,776 A * | 5/1957 | Lipari | A61J 1/2093 206/221 |
| 4,298,207 A * | 11/1981 | Hopper et al. | 277/652 |
| 4,897,207 A * | 1/1990 | Greene | 252/2 |
| 4,986,434 A * | 1/1991 | Prestyly, Jr. | 220/574 |
| 5,337,913 A * | 8/1994 | Fukuda | 220/326 |
| 6,413,668 B1 | 7/2002 | Sandberg et al. | |
| 6,544,614 B1 * | 4/2003 | Huffer et al. | 428/40.1 |
| 2008/0290094 A1 | 11/2008 | Bruce | |
| 2009/0014188 A1 * | 1/2009 | Hesch et al. | 169/48 |
| 2011/0079456 A1 | 4/2011 | Borumand et al. | |

\* cited by examiner

*Primary Examiner* — Fenn Mathew
*Assistant Examiner* — Kevin Castillo
(74) *Attorney, Agent, or Firm* — Walters & Wasylyna LLC

(57) ABSTRACT

A fire extinguishment container including a container body that defines an internal volume and an opening into the internal volume, a cover positionable over the opening, a sealing member positioned between the container body and the cover when the cover is positioned over the opening, wherein the sealing member is formed from a heat-resistant material, and a locking mechanism connected to the container body and the cover to retain the cover over the opening.

27 Claims, 8 Drawing Sheets

FIRE EXTINGUISHMENT CONTAINER

FIELD

This application relates to fire containment and extinguishment and, more particularly, to containers configured to contain and extinguish fires.

BACKGROUND

Consumer electronic devices, such as laptop computers, tablet computers, mobile telephones, smartphones and digital music players, are often powered by rechargeable batteries. While various types of rechargeable batteries are available in the marketplace, lithium-ion batteries are commonly used due to their relatively high energy density and lack of battery memory after a partial charge.

Unfortunately, overheating of lithium-ion batteries, such as overheating caused by overcharging or ambient conditions, has been known to result in thermal runaway. During thermal runaway, lithium-ion batteries may vent gases and, if the thermal runaway continues, may burst into flames. The off-gassing and relatively high combustion temperatures make it difficult to contain and extinguish lithium-ion battery fires.

A lithium-ion battery undergoing thermal runaway is typically moved to a well-ventilated area by appropriate safety personnel, and then the thermal event is allowed to run its course under controlled conditions. Any residual flames may be extinguished using suitable fire extinguishing agents.

Thermal runaway of a lithium-ion battery aboard an aircraft presents a more acute situation. The enclosed space of the passenger cabin of an aircraft offers few options for isolating overheated lithium-ion batteries. Furthermore, overheating of lithium-ion batteries may be difficult to detect aboard cargo aircraft.

Accordingly, those skilled in the art continue with research and development efforts in the field of fire containment and extinguishment, including the containment and extinguishment of fires associated with lithium-ion batteries.

SUMMARY

The disclosed fire extinguishment container may include a container body that defines an internal volume and an opening into the internal volume, a cover positionable over the opening, a sealing member positioned between the container body and the cover when the cover is positioned over the opening, wherein the sealing member is formed from a heat-resistant material, and a locking mechanism connected to the container body and the cover to retain the cover over the opening.

In a variation, the disclosed fire extinguishment container may include a container body that defines an internal volume and an opening into the internal volume, a cover positionable over the opening, wherein the cover defines an elongated opening, a retaining skirt extending at least partially through the elongated opening and defining a compartment within the cover, a fire extinguishing agent received in the compartment, wherein the fire extinguishing agent is released from the compartment to the internal volume when the retaining skirt is drawn from the cover through the elongated opening, a sealing member positioned between the container body and the cover when the cover is positioned over the opening, and a locking mechanism connected to the container body and the cover to retain the cover over the opening.

In another variation, also disclosed is a method for containing an object, such as a lithium-ion battery undergoing a thermal event. The method may include the steps of (1) providing a container, the container including a heat-resistant cover that may be sealingly mated with a heat-resistant container body, wherein the cover initially houses a fire extinguishing agent, (2) placing the object into the gas-tight container, and (3) releasing the fire extinguishing agent from the cover into the container body.

Other variations and alternatives of the disclosed fire extinguishment container and method will become apparent from the following detailed description, the accompanying drawings and the appended claims.

DETAILED DESCRIPTION

Disclosed is a fire extinguishment container that may be used to isolate and contain one or more items undergoing a thermal event, such as a lithium-ion battery undergoing thermal runaway. Those skilled in the art will appreciate that the present disclosure is equally useful for lithium-polymer, lithium-ion polymer, and other lithium metal-containing batteries. The disclosed fire extinguishment container may be particularly advantageous for use on aircraft, where there are few options for safely isolating and containing items undergoing a thermal event. However, those skilled in the art will appreciate that the disclosed fire extinguishment container may also be useful in various non-aerospace applications, such as in the home, school or office.

Figure 1:
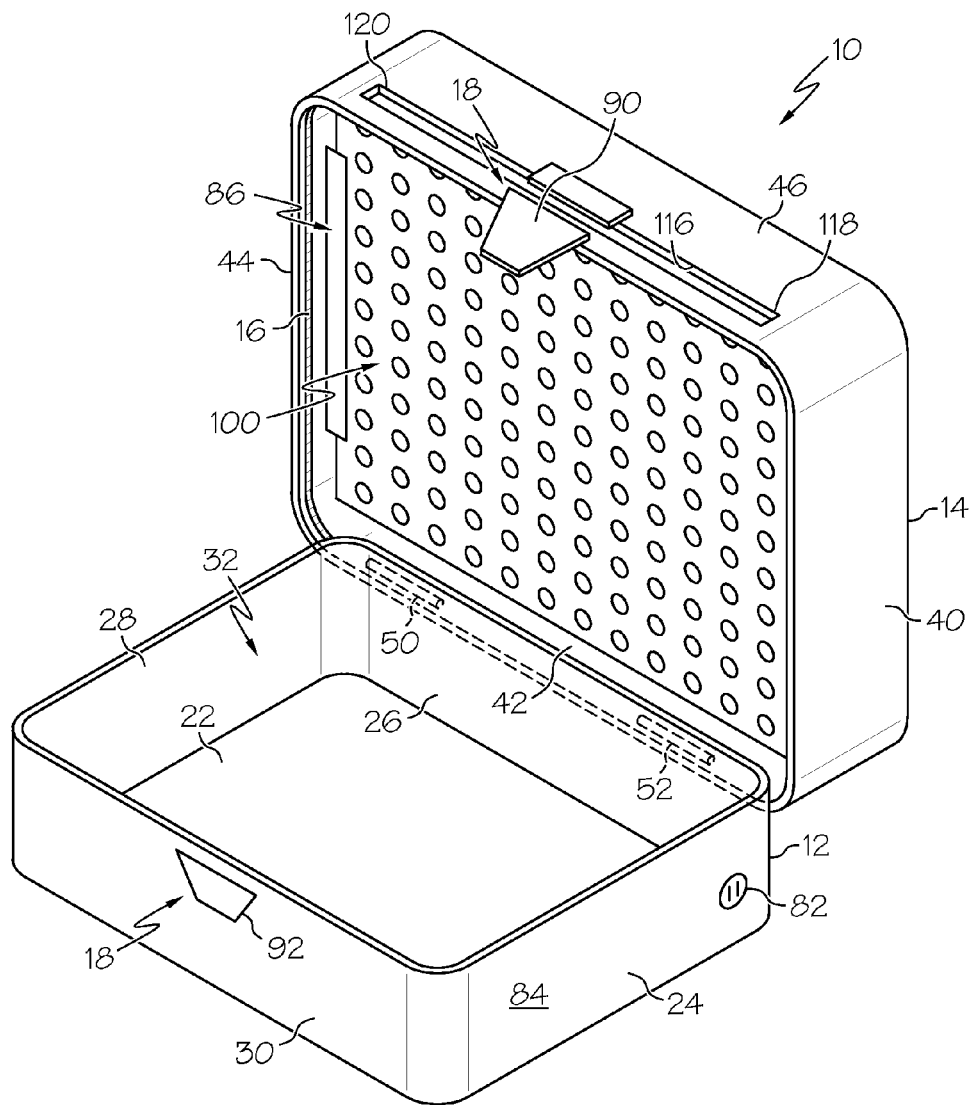
FIG. 1 is a front and top perspective view of one variation of the disclosed fire extinguishment container.
Figure 2:
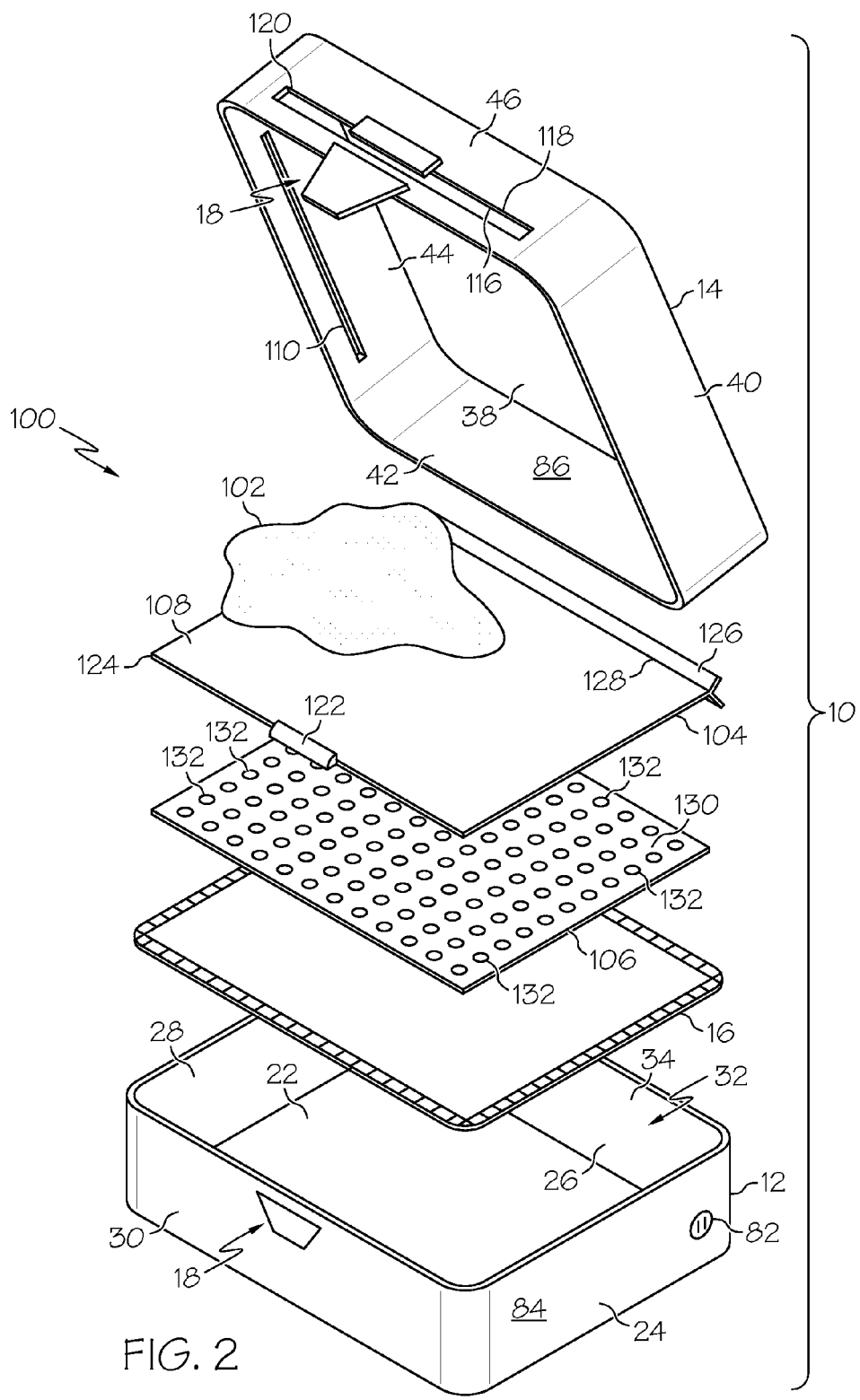
FIG. 2 is an exploded perspective view of the fire extinguishment container of FIG. 1.

Referring to FIGS. 1 and 2, one embodiment of the disclosed fire extinguishment container, generally designated 10, may include a container body 12, a cover 14, a sealing member 16 and a locking mechanism 18. The fire extinguishment container 10 may include additional features and components, such as the fire extinguishment assembly described below, without departing from the scope of the present disclosure.

The container body 12 may include a base wall 22 and four side walls 24, 26, 28, 30. The four side walls 24, 26, 28, 30 may extend upward from the base wall 22 to define an internal volume 32 of the container body 12 and a mouth or opening 34 into the internal volume 32. In one expression, the base wall 22 and the side walls 24, 26, 28, 30 may be formed as separate pieces that have been connected together (e.g., by welding) to form the container body 12. In another expression, the base wall 22 and the four side walls 24, 26, 28, 30 of the container body 12 may be formed as a single, monolithic piece (e.g., by stamping or molding).

While the container body 12 is shown and described as having four side walls 24, 26, 28, 30 that provide the container body 12 with a generally rectilinear shape in top view, the container body 12 may be constructed in various shapes and configurations. As one alternative example, the container body 12 may have fewer than four side walls or more than four side walls. As another alternative example, the container body 12 may include one continuous side wall that provides the container body 12 with a circular or oval shape.

Figure 6:
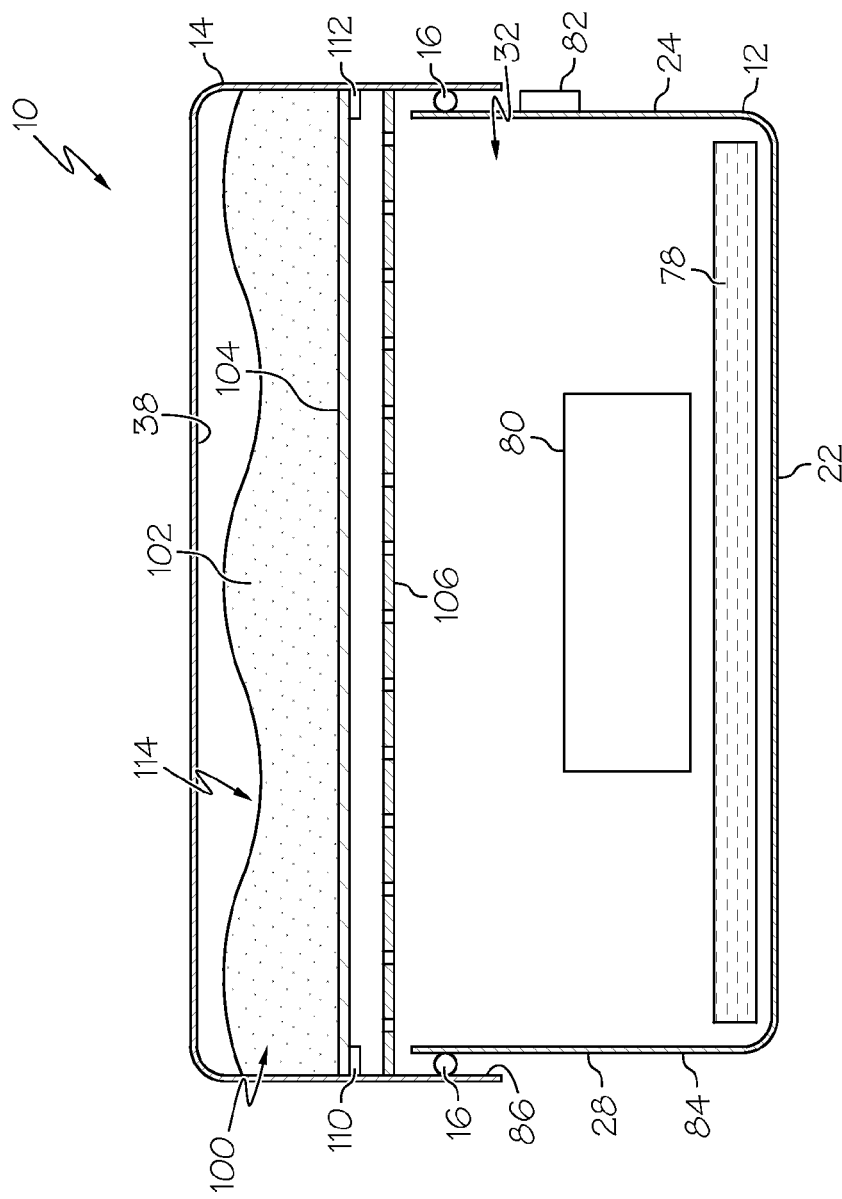
FIG. 6 is a front elevational view, in section, of the fire extinguishment container of FIG. 1, shown in a closed configuration.

The cover 14 may include an upper wall 38 and four side walls 40, 42, 44, 46. The four side walls 40, 42, 44, 46 may extend downward from the upper wall 38 such that the side walls 40, 42, 44, 46 of the cover 14 are at least partially received over the side walls 24, 26, 28, 30 of the container body 12 when the cover 14 is sealingly mated with the container body 12, as shown in FIG. 6. Like the container body 12, the cover 14 may be formed from multiple connected pieces or as a single, monolithic piece.

Thus, as shown in FIG. 6, the cover 14 may be closely received over the container body 12 to enclose the internal volume 32 of the container body 12.

Figure 7:
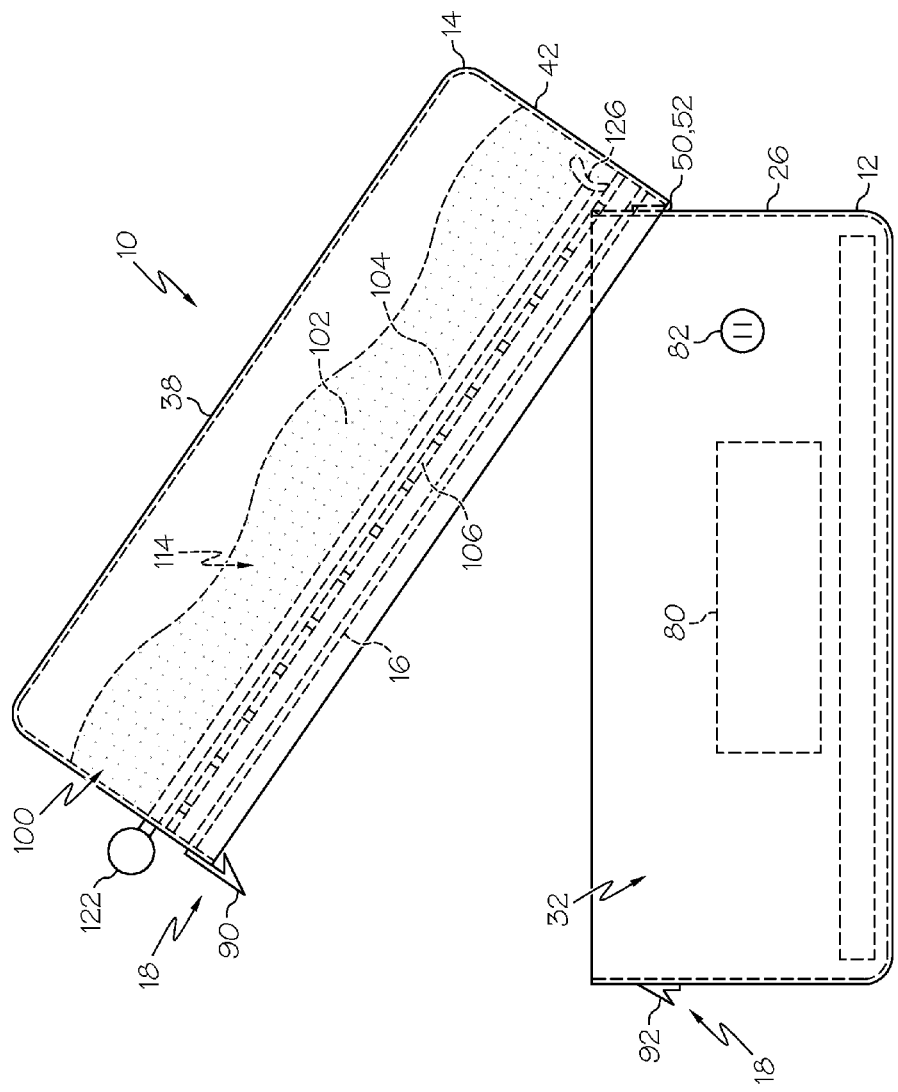
FIG. 7 is side elevational view of the fire extinguishment container of FIG. 1, shown in an open configuration.

As best shown in FIGS. 1 and 7, the cover 14 may be hingedly connected to the container body 12 to provide the fire extinguishment container 10 with a clamshell-like structure. For example, hinges 50, 52 may connect the rear wall 26 of the container body 12 to the rear wall 42 of the cover 14 such that the cover 14 may pivot relative to the container body 12 between a first, open configuration, shown in FIGS. 1 and 7, and second, closed configuration, shown in FIGS. 6 and 8. Other techniques for effecting a hinged connection between the cover 14 and the container body 12 are also contemplated, and are within the purview of those skilled in the art.

The walls 22, 24, 26, 28, 30 of the container body 12 and the walls 38, 40, 42, 44, 46 of the cover 14 may be constructed from various fire-resistant materials. To ensure structural integrity, the selected fire-resistant material may be relatively rigid and relatively hard (i.e., not brittle), and may maintain hardness and rigidity at high temperatures, such as temperatures in excess of 1,000° F.

Figure 3:
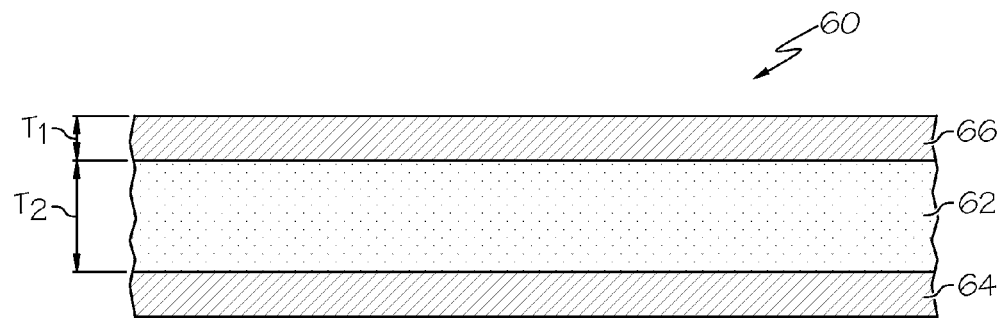
FIG. 3 is a cross-sectional view of one construction of a portion of the fire extinguishment container of FIG. 1.

In one construction, one or more walls 22, 24, 26, 28, 30, 38, 40, 42, 44, 46 of the fire extinguishment container 10 may be formed as a layered structure 60, as shown in FIG. 3. The layered structure 60 may include an insulating layer 62 positioned between two structural layers 64, 66. Additional layers, such as additional insulating layers and/or additional structural layers, may be included in the layered structure 60 without departing from the scope of the present disclosure.

The structural layers 64, 66 may be formed from various fire-resistant materials, such as metal. For example, the structural layers 64, 66 may be formed from steel, such as stainless steel, high-temperature aluminum alloys, titanium alloys or the like. Use of non-metallic materials, such as graphite and ceramic materials, for the structural layers 64, 66 is also contemplated.

The structural layers 64, 66 may have a cross-sectional thickness $T_1$ sufficient to provide strength and rigidity to the walls 22, 24, 26, 28, 30, 38, 40, 42, 44, 46 of the fire extinguishment container 10. Those skilled in the art will appreciate that the cross-sectional thickness $T_1$ of the structural layers 64, 66 may depend on a variety of factors, including material selection and weight considerations. In one expression, the cross-sectional thickness $T_1$ of each structural layer 64, 66 may be at least about 0.4 millimeters. In another expression, the cross-sectional thickness $T_1$ of each structural layer 64, 66 may be at least about 0.6 millimeters. In another expression, the cross-sectional thickness $T_1$ of each structural layer 64, 66 may be at least about 0.8 millimeters. In yet another expression, the cross-sectional thickness $T_1$ of each structural layer 64, 66 may be at least 1 millimeter.

The insulating layer 62 may be formed from various insulating materials, such as non-combustible insulating materials. One example of a suitable non-combustible insulating material for forming the insulating layer 62 is mineral wool. Another example of a suitable non-combustible insulating material for forming the insulating layer 62 is fiberglass. Yet another example of a suitable non-combustible insulating material for forming the insulating layer 62 is stone wool. Use of other non-combustible insulating materials is also contemplated.

The insulating layer 62 may have a cross-sectional thickness $T_2$ sufficient to minimize heat transfer between the structural layers 64, 66. Those skilled in the art will appreciate that the cross-sectional thickness $T_2$ of the insulating layer 62 may depend on a variety of factors, including the type of insulating material used. In one expression, the cross-sectional thickness $T_2$ of the insulating layer 62 may be at least about 0.125 inches. In another expression, the cross-sectional thickness $T_2$ of the insulating layer 62 may be at least about 0.25 inches. In another expression, the cross-sectional thickness $T_2$ of the insulating layer 62 may be at least about 0.5 inches. In yet another expression, the cross-sectional thickness $T_2$ of the insulating layer 62 may be at least about 1 inch.

Figure 4:
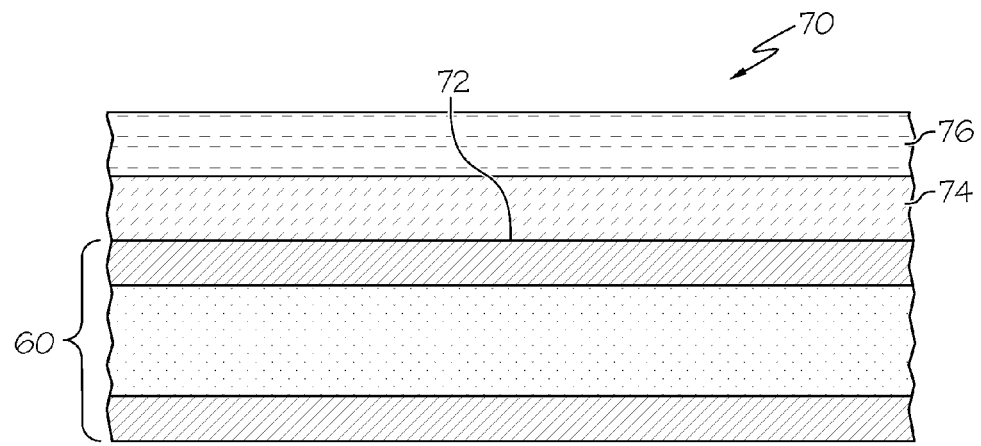
FIG. 4 is a cross-sectional view of another construction of a portion of the fire extinguishment container of FIG. 1.

In another construction, one or more walls 22, 24, 26, 28, 30, 38, 40, 42, 44, 46 of the fire extinguishment container 10 may be formed as a layered structure 70, as shown in FIG. 4. The layered structure 70 may include the layered structure 60 of FIG. 3, and the inner surface 72 of the layered structure 60 may include a reinforcing layer 74, a heat-resistant layer 76 or both a reinforcing layer 74 and a heat-resistant layer 76.

The reinforcing layer 74 may include a high strength reinforcing material, such as ballistic fiber, particularly fire-resistant ballistic fiber. As one example, the reinforcing layer 74 may include meta-aramid fiber, such a NOMEX® brand fiber available from E. I. du Pont de Nemours and Company of Wilmington, Del. As another example, the reinforcing layer 74 may include para-aramid fiber, such a KEVLAR® brand fiber, also available from E. I. du Pont de Nemours and Company.

Without being limited to any particular theory, it is believed that incorporating a reinforcing layer 74, such as a reinforcing layer 74 that includes an aramid fiber, into one or more walls 22, 24, 26, 28, 30, 38, 40, 42, 44, 46 of the fire extinguishment container 10 may at least partially contain any flying debris or shrapnel that may result from over-pressurization within the fire extinguishment container 10 or an explosion within the fire extinguishment container 10.

The heat-resistant layer 76 may include one or more heat-resistant materials. As one example, the heat-resistant layer 76 may be formed from or may include welding blanket material, such fiberglass. As another example, the heat-resistant layer 76 may be formed from or may include a carbonaceous material, such graphite or carbon fiber. As another example, the heat-resistant layer 76 may be formed from or may include leather.

In yet another construction, both layered structure 60 (FIG. 3) and layered structure 70 (FIG. 4) may be used to construct the fire extinguishment container 10. For example, the base wall 22 of the container body 12 and the side walls 40, 42, 44, 46 of the cover 14 may be constructed from the layered structure 60 shown in FIG. 3, while the upper wall 38 of the cover 14 and the side walls 24, 26, 28, 30 of the container body 12 may be constructed from the layered structure 70 shown in FIG. 4. Various other constructions are also contemplated.

Referring to FIG. 6, an optional base member 78 may be positioned in the container body 12 to cover all (or a portion) of the base wall 22 of the container body 12. The base member 78 may provide a thermal barrier between the base wall 22 of the container body 12 and an object 80 (e.g., a lithium-ion battery) positioned in the internal volume 32 of the container body 12. Therefore, the base member 78 may support the object 80 placed into the fire extinguishment container 10, and may ensure that the object 80 is not in direct contact with the base wall 22 of the container body 12. Those skilled in the art will appreciate that spacing of the object 80 from the base wall 22 of the container body 12 may be particularly advantageous when the object 80 is undergoing a thermal event (e.g., thermal runaway or fire).

The base member 78 may be formed from one or more fire-resistant materials. Since the base member 78 may be in direct contact with an object 80 undergoing a thermal event, the base member 78 may be capable of withstanding temperatures in excess of 1000° F. In one expression, the base member 78 may be capable of withstanding temperatures in excess of 1200° F. In another expression, the base member 78 may be capable of withstanding temperatures in excess of 1400° F. In another expression, the base member 78 may be capable of withstanding temperatures in excess of 1600° F. In another expression, the base member 78 may be capable of withstanding temperatures in excess of 1800° F. In yet another expression, the base member 78 may be capable of withstanding temperatures in excess of 2000° F.

A variety of fire-resistant materials may be used to form the base member 78. As one non-limiting example, the base member 78 may be a ceramic tile or plate. As another non-limiting example, the base member 78 may be stone, such as a stone tile. As another non-limiting example, the base member 78 may be brick. As yet another non-limiting example, the base member 78 may be an aramid fiber material (e.g., para-aramid). Other examples of suitable fire-resistant materials will become apparent to those skilled in the art.

Figure 5:
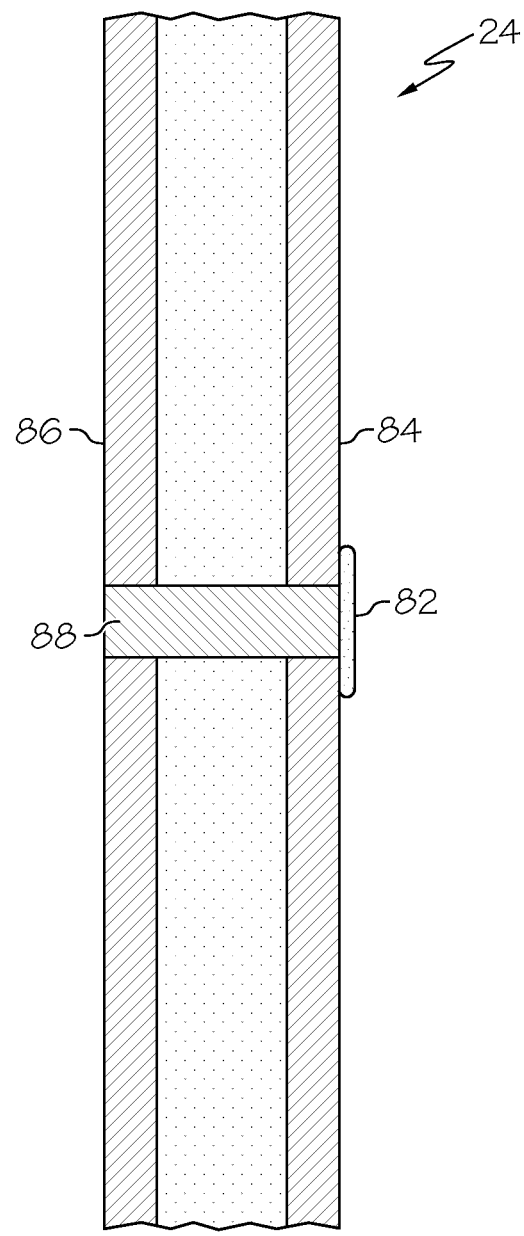
FIG. 5 is a cross-sectional view of a temperature sensing device incorporated into the fire extinguishment container of FIG. 1.

Referring to FIGS. 1 and 5, the fire extinguishment container 10 may optionally include a temperature sensing device 82 configured to provide a visual indication (or at least an approximation) of the temperature within the fire extinguishment container 10 (i.e., within the internal volume 32 of the container body 12) or a visual indication that the temperature within the fire extinguishment container 10 has exceed a threshold level (e.g., 500° F.). For example, the temperature sensing device 82 may be mounted on the external surface 84 of the container body 12 such that the temperature sensing device 82 may be observed while the fire extinguishment container 10 is in the closed configuration (FIG. 6).

As discussed above, the walls 22, 24, 26, 28, 30, 38, 40, 42, 44, 46 of the fire extinguishment container 10 may be thermally insulated. Therefore, as shown in FIG. 5, a thermally conductive coupling member 88, such as a metal plug or probe, may extend through the associated wall 24 of the fire extinguishment container 10 to thermally couple the temperature sensing device 82 on the external surface 84 with the internal surface 86 of the fire extinguishment container 10. Also contemplated is the use of temperature sensing devices that extend through the walls of the fire extinguishment container 10 without the need for a coupling member 88.

In one implementation, the temperature sensing device 82 may include one or more heat sensitive materials that provide a visual indication (e.g., change color) if the heat sensitive material is exposed to temperatures in excess of a threshold temperature. For example, the temperature sensing device 82 may be a heat sensor label that turns black when exposed to temperatures in excess of 300° F., such as a CHIEF heat sensor label for fire ladders available from Chief, Inc. of Charlotte, N.C.

Alternatively, the temperature sensing device 82 may include a temperature probe, a thermometer, a thermocouple or the like that provides an indication of actual temperature in real-time (or close to real-time). The actual temperature may be indicted with an analog display or a digital read-out. Optionally, the temperature sensing device 82 may include an alarm set to trigger when the sensed temperature exceeds a pre-determined threshold value (e.g., 300° F.).

Referring now to FIGS. 1, 2 and 6, the sealing member 16 may provide a substantially gas-tight seal between the cover 14 and the container body 12 when the fire extinguishment container 10 is in the closed configuration (FIG. 6). Therefore, the sealing member 16 may inhibit (i.e., may reduce if not eliminate) the release of gases from the closed fire extinguishment container 10, such as when an object 80 (FIG. 6) positioned within the internal volume 32 of the closed fire extinguishment container 10 is off-gassing while undergoing a thermal event.

The sealing member 16 may be connected to the internal surface 86 of the side walls 40, 42, 44, 46 of the cover 14, as best shown in FIG. 1, and may extend substantially entirely (e.g., continuously) around the internal surface 86 of the side walls 40, 42, 44, 46 of the cover 14. Therefore, as shown in FIG. 6, the sealing member 16 may be compressed between the external surface 84 of the side walls 24, 26, 28, 30 of the container body 12 and the internal surface 86 of the side walls 40, 42, 44, 46 of the cover 14 when the fire extinguishment container 10 is in the closed configuration.

The sealing member 16 may be formed from a flexible, heat-resistant material. In one particular construction, the sealing member 16 may be a gasket-type sealing member, and may include fiberglass rope, such as fiberglass rope typically used as a door gasket in connection with wood stoves, kilns and the like. Various fiberglass ropes suitable for forming the sealing member 16 are available from AB Thermal Technologies of Evans Mills, N.Y.

While the sealing member 16 is described as being a gasket-type sealing member, other variations are also contemplated. Those skilled in the art will appreciate that the sealing member 16 may be any device, structure, apparatus or system capable of providing a generally gas-tight seal between the cover 14 and the container body 12. For example, the sealing member 16 may alternatively be a compression-type seal.

Figure 8:
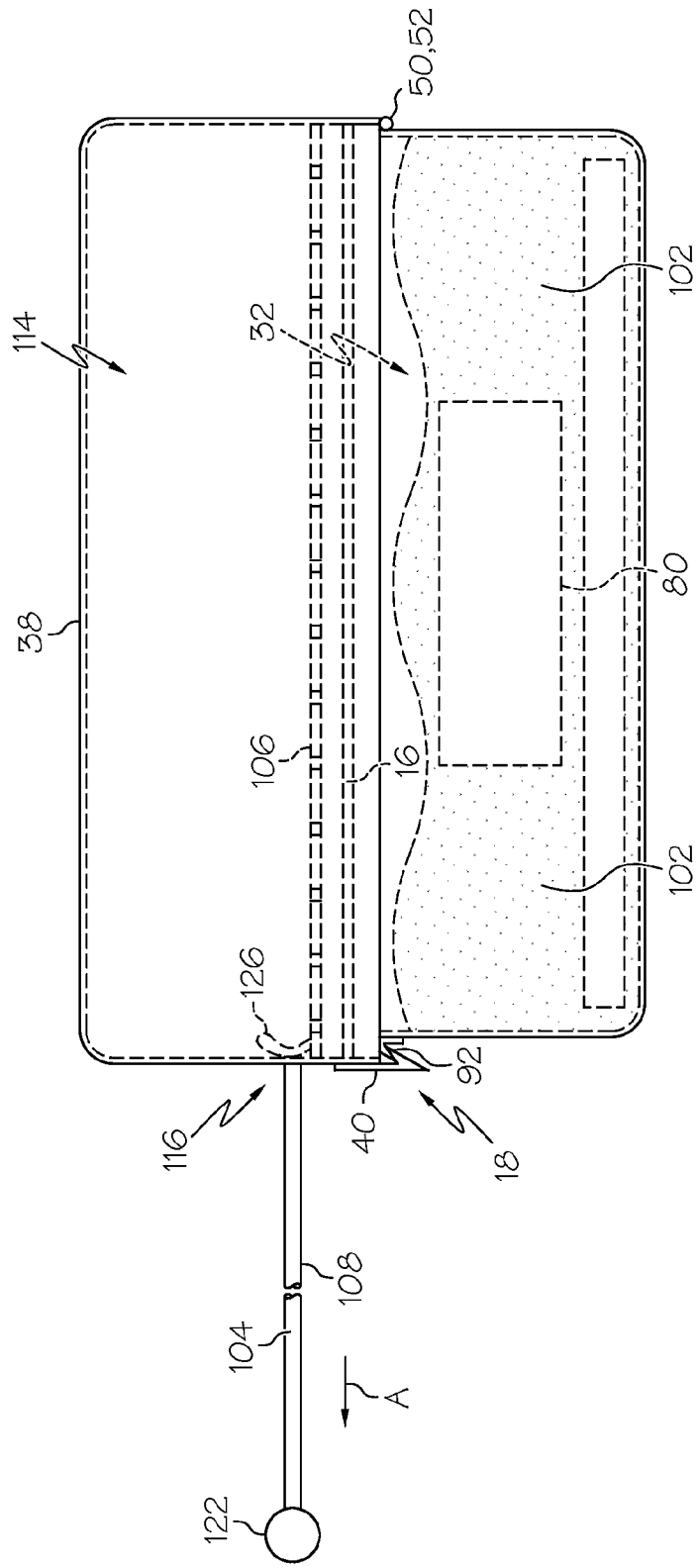
FIG. 8 is side elevational view of the fire extinguishment container of FIG. 7, shown in a closed and deployed configuration.

Referring now to FIGS. 1, 7 and 8, the locking mechanism 18 may ensure that the cover 14 remains sealingly engaged with the container body 12 when the fire extinguishment container 10 is in the closed configuration (FIG. 8). The locking mechanism 18 may maintain sealing engagement between the cover 14 and the container body 12 even during pressurization of the closed fire extinguishment container 10, such as when an object 80 (FIG. 8) positioned within the internal volume 32 of the closed fire extinguishment container 10 is off-gassing while undergoing a thermal event.

The locking mechanism 18 may include a hook (or latch) member 90 and a catch member 92. The hook member 90 may be connected to the front side wall 46 of the cover 14 and the catch member 92 may be connected to the front side wall 30 of the container body 12. The connection between the hook member 90 and the front side wall 46 of the cover 14 may be a pivoting connection to facilitate release of the locking mechanism 18 when it is desired to open the closed fire extinguishment container 10.

Thus, as shown in FIGS. 7 and 8, the cover 14 may pivot relative to the container body 12 at the hinges 50, 52, thereby approximating the cover 14 with the container body 12. As the cover 14 approximates the container body 12, the hook member 90 may approximate and, eventually, latch onto the catch member 92, thereby locking the cover 14 in sealing engagement with the container body 12. Therefore, optionally, the locking mechanism 18 may automatically lock the cover 14 onto the container body 12 whenever the cover 14 is brought into sealing engagement with the container body 12.

At this point, those skilled in the art will appreciate that locking mechanisms 18 having a hook member 90 and a catch member 92 are just one of many suitable locking mechanisms that may be used to secure the cover 14 in sealing engagement with the container body 12. Various other locking mechanisms, such slide latches, bolts, hook-and-loop mechanisms, spring-loaded detents, straps, belts, ratcheting tie-downs and the like, may be used without departing from the scope of the present disclosure. Those skilled in the art will also appreciate that using just one locking mechanism 18 may not always be suitable. For example, multiple spaced-apart locking mechanisms 18 may be used, particularly when the cover 14 is not hingedly connected to the container body 12.

Optionally, the fire extinguishment container 10 may include a pressure release valve. The pressure release valve may be connected to the container body 12 and/or the cover 14, and may be configured to release pressure (e.g., release gases) from the container 10 through the pressure release valve when the pressure within the container 10 exceeds a predetermined threshold value.

Referring now to FIGS. 1, 2 and 6-8, the disclosed fire extinguishment container 10 may include a fire extinguishment assembly, generally designated 100, that may include a fire extinguishing agent 102, a retaining skirt 104 and, optionally, a distribution panel 106. The retaining skirt 104 may initially retain the fire extinguishing agent 102 within the cover 14 of the fire extinguishment container 10, as shown in FIGS. 6 and 7. Then, when the fire extinguishment assembly 100 is deployed, the fire extinguishing agent 102 may be released into the internal volume 32 of the container body 12 to act on an object 80 housed in the internal volume 32, as shown in FIG. 8.

The fire extinguishing agent 102 may be any composition capable of extinguishing or otherwise controlling a fire. Those skilled in the art will appreciate that the composition of the fire extinguishing agent 102 may be dictated by the type of fire (e.g., lithium-ion battery fire) to be extinguished by the fire extinguishing agent 102. Therefore, a variety of different fire extinguishing agents may be used without departing from the scope of the present disclosure.

In a first realization, the fire extinguishing agent 102 may be a Class D fire extinguishing agent. Use of Class D fire extinguishing agents may be particularly suitable when the disclosed fire extinguishment container 10 is intended for use with lithium-ion batteries. Several general, non-limiting examples of suitable Class D fire extinguishing agents include sodium chloride, sodium carbonate, sand, graphite powder and copper powder. One specific example of a suitable Class D fire extinguishing agent is Super D dry powder available from Amerex Corporation of Trussville, Ala.

In a second realization, the fire extinguishing agent 102 may be a liquid fire extinguishing agent. One non-limiting example of a suitable liquid fire extinguishing agent is water.

In a third realization, the fire extinguishing agent 102 may be a foam-based fire extinguishing agent. One non-limiting example of a suitable foam-based fire extinguishing agent is aqueous film forming foam.

In a fourth realization, the fire extinguishing agent 102 may be a gaseous fire extinguishing agent. One non-limiting example of a suitable gaseous fire extinguishing agent is carbon dioxide. Another non-limiting example of a suitable gaseous fire extinguishing agent is bromotrifluoromethane, which is also known as Halon gas.

The fire extinguishing agent 102 may be retained within the cover 14 of the fire extinguishment container 10 by the retaining skirt 104. As best shown in FIG. 2, the retaining skirt 104 may include a generally planar body 108 formed from a substantially rigid material, such as sheet metal (e.g., steel). The body 108 of the retaining skirt 104 may be sized and shape to be closely received between the side walls 42, 44, 46, 48 of the cover 14, as shown in FIG. 6. Rails 110, 112 may retain the body 108 of the retaining skirt 104 within the cover 14, and in a configuration such that the body 108 is substantially parallel with the upper wall 38 of the cover 14. The body 108 of the retaining skirt 104 may be slidably received over the rails 110, 112 (or between a pair of closely spaced rails (not shown).

Thus, the body 108 of the retaining skirt 104 and the upper and side walls 38, 40, 42, 44, 46 of the cover 14 may define a compartment 114 within the cover 14. Therefore, prior to deployment of the fire extinguishment assembly 100, the fire extinguishing agent 102 may be housed within the compartment 114.

As best shown in FIGS. 1 and 2, the front wall 46 of the cover 14 may define an opening 116. The opening 116 may be elongated across the front wall 46 of the cover 14, and may extend from a first end 118 proximate the right side wall 40 of the cover 14 to a second end 120 proximate the left side wall 44 of the cover 14. The opening 116 may be substantially aligned with the retaining skirt 104, and may be sized and shaped to allow the body 108 of the retaining skirt 104 to pass therethrough.

As best shown in FIGS. 2 and 7, a gripping portion 122, such as a handle, may be connected to the forward edge 124 (FIG. 2) of the body 108 of the retaining skirt 104. The gripping portion 122 may be positioned outside of the cover 14.

Accordingly, a user may grasp the retaining skirt 104 by the gripping portion 122 and may pull the body 108 of the retaining skirt 104 through the opening 116 in the cover 14 in the direction shown by arrow A, as shown in FIG. 8. As the retaining skirt 104 is pulled through the opening 116, the fire extinguishing agent 102 may be released from the compartment 114 and may drop down into the internal volume 32 of the container body 12 under the force of gravity, thereby allowing the fire extinguishing agent 102 to act on the object 80 (if any) housed within the fire extinguishment container 10.

As shown in FIGS. 2, 7 and 8, a sealing member 126 may be connected to the rear edge 128 (FIG. 2) of the body 108 of the retaining skirt 104. Therefore, as shown in FIG. 8, the sealing member 126 may seal the opening 116 in the cover 14 when the retaining skirt 104 has been fully withdrawn from the cover 14, thereby reducing or eliminating the risk that gases may escape from the fire extinguishment container 10 through the opening 116.

Optionally, a locking mechanism may be provided to lock the retaining skirt 104 in the withdrawn configuration once the retaining skirt 104 has been pulled through the opening 116. For example, the locking mechanism may include a detent or a one-way ratcheting system that allows the retaining skirt 104 to be withdrawn from the cover 14, but prevents the retaining skirt 104 from being urged back into the cover 14 after it has been withdrawn. Therefore, the locking mechanism prevent the retaining skirt 104 from unintentionally being reinserted into the cover 14, which may break the seal between the cover 14 and the sealing member 126 associated with the retaining skirt 104.

The sealing member 126 may be formed from a flexible, heat-resistant material, such the heat-resistant material used to form the sealing member 16, and may be sized and shaped to fill the opening 116 in the cover 14. As one specific example, the sealing member 126 may be fiberglass rope.

The distribution panel 106 may be positioned below the retaining skirt 104 (i.e., the retaining skirt 104 may be positioned between the distribution panel 106 and the upper wall 38 of the cover 14). Therefore, the fire extinguishing agent 102 released from the compartment 114 when the retaining skirt 104 is withdrawn (arrow A in FIG. 8) must pass through the distribution panel 106 before dropping down into the internal volume 32 of the container body 12. As such, the distribution panel 106 may ensure that the entire charge of fire extinguishing agent 102 housed in the compartment 114 does not all drop at once as the retaining skirt 104 is withdrawn, but rather distributes the fire extinguishing agent 102 more evenly into the internal volume 32 of the container body 12.

As best shown in FIG. 2, the distribution panel 106 may include a generally planar body 130 that defines a plurality of openings 132, such as holes, perforations of the like. Those skilled in the art will appreciate that the size, shape, angle or other configurations of the openings 132 may be dictated by, among other considerations, the flowability of the fire extinguishing agent 102 used. For example, smaller openings 132 may be used for fire extinguishing agents 102 that more readily flow. The openings 132 may be arranged in various uniform or random patterns.

The distribution panel 106 may be sized and shape to be closely received between the side walls 42, 44, 46, 48 of the cover 14, as shown in FIG. 6. Indeed, the distribution panel 106 may be fixedly connected to the side walls 42, 44, 46, 48 of the cover 14. Therefore, when the retaining skirt 104 is withdrawn, as shown in FIG. 8, the fire extinguishing agent 102 released from the compartment 114 may pass through the openings 132 in the distribution panel 106 before dropping down into the internal volume 32 of the container body 12.

Figure 9:
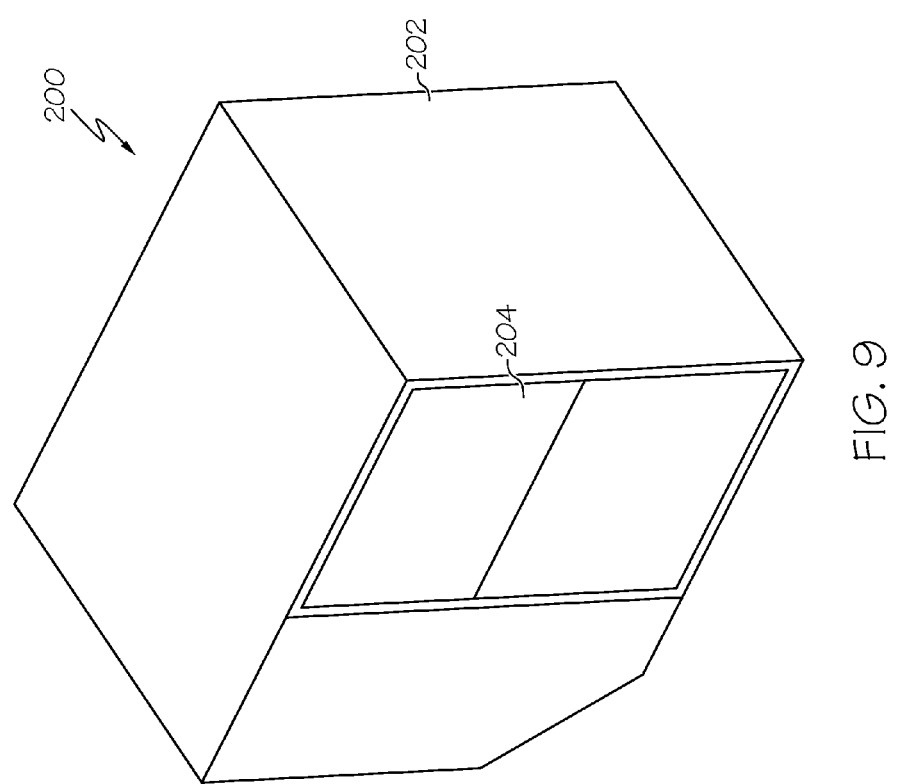
FIG. 9 is a front perspective view of another variation of the disclosed fire extinguishment container.

Referring to FIG. 9, another embodiment of the disclosed fire extinguishment container, generally designated 200, may be constructed as an aircraft cargo container. Due to its size, the fire extinguishment container 200 may be particularly suitable for transporting large quantities of objects, such as a pallet of lithium-ion batteries.

Like the relatively smaller fire extinguishment container 10, the fire extinguishment container 200 may include a container body 202 and a cover 204. A sealing member (not shown in FIG. 9) may ensure a substantially gas-tight seal between the cover 204 and the container body 202. A locking mechanism (not shown in FIG. 9) may ensure that the cover 204 remains in sealing engagement with the container body 202 even when the internal volume of the fire extinguishment container 200 is pressurized, such as when an object housed within the fire extinguishment container 200 is undergoing a thermal event.

Thus, despite the significantly larger size of the fire extinguishment container 200 relative to the fire extinguishment container 10, the fire extinguishment container 200 may be constructed in a similar manner. However, depending on overall size, incorporating a fire extinguishment assembly, as described above, into the fire extinguishment container 200 may prove unfeasible, as will be appreciated by those skilled in the art.

Accordingly, the disclosed fire extinguishment containers may be used to isolate and contain various objects, such as lithium-ion batteries, undergoing a thermal event. Specifically, the insulated walls of the disclosed fire extinguishment containers may contain the heat released during a thermal event, the heat-resistant seals may inhibit the escape of gases released during a thermal event, and the optional fire extinguishment assembly may extinguish or control any resulting fires. Therefore, the disclosed fire extinguishment containers may provide a safety option in various aerospace and non-aerospace applications.

Although variations of the disclosed fire extinguishment container have been shown and described, modifications may occur to those skilled in the art upon reading the specification. The present application includes such modifications and is limited only by the scope of the claims.

What is claimed is:

1. A fire extinguishment container comprising:
    a container body that defines an internal volume and an opening into said internal volume;
    a cover positionable over said opening, said cover defining an elongated opening;
    a sealing member positioned between said container body and said cover when said cover is positioned over said opening, wherein said sealing member is formed from a heat-resistant material;
    a locking mechanism connected to said container body and said cover to retain said cover over said opening; and
    a retaining skirt sized and shaped to pass through said elongated opening, said retaining skirt and said cover defining a compartment within said cover, wherein said compartment is isolated from said internal volume when said retaining skirt is in a closed position, and wherein said retaining skirt is moveable to an open position by pulling said retaining skirt from said cover through said elongated opening.

2. The container of claim 1 wherein said container body comprises a base wall and a plurality of side walls that define said internal volume.

3. The container of claim 2 wherein said cover comprises an upper wall and a plurality of side walls.

4. The container of claim 3 wherein said sealing member is positioned between said plurality of side walls of said container body and said plurality of side walls of said cover when said cover is positioned over said opening.

5. The container of claim 1 wherein said cover is hingedly connected to said container body.

6. The container of claim 1 wherein said container body is formed from a layered structure comprising an insulating layer positioned between a first structural layer and a second structural layer.

7. The container of claim 6 wherein said insulating layer comprises a non-combustible insulating material.

8. The container of claim 7 wherein said non-combustible insulating material is selected from the group consisting of mineral wool, fiberglass and stone wool.

9. The container of claim 6 wherein said first and said second structural layers comprise metal.

10. The container of claim 6 wherein said layered structure further comprises a reinforcing layer.

11. The container of claim 10 wherein said reinforcing layer comprises aramid fibers.

12. The container of claim 6 wherein said layered structure further comprises a heat-resistant layer, and wherein said heat-resistant layer is the innermost layer of the layered structure.

13. The container of claim 1 further comprising a base member positioned in said internal volume.

14. The container of claim 13 wherein said base member comprises a material selected from the group consisting of ceramic, stone, brick and aramid fiber.

15. The container of claim 1 further comprising a temperature sensing device connected to at least one of said container body and said cover.

16. The container of claim 15 wherein said temperature sensing device comprises a heat sensor label.

17. The container of claim 1 wherein said sealing member is compressed between said container body and said cover when said cover is positioned over said opening.

18. The container of claim 1 wherein said sealing member is connected to said cover.

19. The container of claim 1 wherein said heat-resistant material comprises fiberglass.

20. The container of claim 1 wherein said sealing member comprises fiberglass rope.

21. The container of claim 1 wherein said locking mechanism comprises a hook member connected to one of said container body and said cover, and a catch member connected to the other of said container body and said cover.

22. The container of claim 1 further comprising a fire extinguishing agent received in said compartment, wherein said fire extinguishing agent is released from said compartment to said internal volume when said retaining skirt is moved to said open position.

23. The container of claim 1 further comprising a distribution panel connected to said cover, said distribution panel defining a plurality of openings.

24. The container of claim 23 further comprising a fire extinguishing agent received in said compartment, wherein said fire extinguishing agent passes through said plurality of opening when said retaining skirt is moved to said open position.

25. The container of claim 1 wherein said retaining skirt comprises a second sealing member, and wherein said second sealing member seals said elongated opening when said retaining skirt is moved to said open position.

26. The container of claim 22 wherein said fire extinguishing agent is a Class D fire extinguishing agent.

27. The container of claim 1 further comprising a lithium-ion battery received in said internal volume.

* * * * *